United States Patent [19]

Sievers et al.

[11] Patent Number: 6,095,134
[45] Date of Patent: Aug. 1, 2000

[54] METHODS AND APPARATUS FOR FINE PARTICLE FORMATION

[75] Inventors: Robert E. Sievers, Boulder, Colo.; Uwe Karst, Muenster, Germany

[73] Assignee: The Board of Regents of the University of Co, Boulder, Colo.

[21] Appl. No.: 08/847,310

[22] Filed: Apr. 24, 1997

Related U.S. Application Data

[60] Division of application No. 08/224,764, Apr. 8, 1994, Pat. No. 5,639,441, which is a continuation-in-part of application No. 07/846,331, Mar. 6, 1992, Pat. No. 5,301,664.

[51] Int. Cl.$^7$ .................................................. A61M 11/00
[52] U.S. Cl. ................................ 128/200.14; 128/200.23
[58] Field of Search ........................ 128/200.14, 203.12, 128/203.15, 200.23; 424/45, 46, 9.1, 9.3, 401, 489, 450; 427/255.1, 255.6; 222/635; 252/305, 312, 314, 319, 309; 210/634, 639, 635, 638, 656, 659, 643; 435/178, 180, 182; 514/202, 2, 21; 530/412, 418, 419, 427, 413, 417, 38.5; 526/207

[56] References Cited

U.S. PATENT DOCUMENTS

| | | | |
|---|---|---|---|
| 2,524,590 | 10/1950 | Boe | 252/305 |
| 2,908,442 | 10/1959 | Stone | 239/2 |
| 3,159,535 | 12/1964 | Sesso et al. | 167/39 |

(List continued on next page.)

FOREIGN PATENT DOCUMENTS

| | | |
|---|---|---|
| 0 008 454 | 8/1979 | European Pat. Off. . |
| 0 040 887 A1 | 12/1981 | European Pat. Off. . |
| 0 081 014 | 6/1983 | European Pat. Off. . |
| 0 370 268 A2 | 5/1990 | European Pat. Off. . |
| 0 388 927 A1 | 9/1990 | European Pat. Off. . |
| 0 677 332 A3 | 10/1995 | European Pat. Off. . |
| 2 501 644 | 3/1981 | France . |
| 4323666 A1 | of 0000 | Germany . |
| 1591990 A1 | 10/1987 | U.S.S.R. . |
| 1577796 A1 | 9/1988 | U.S.S.R. . |
| WO 90/03782 | 4/1990 | WIPO . |
| WO 90/07351 | 7/1990 | WIPO . |
| WO 90/15635 | 12/1990 | WIPO . |

OTHER PUBLICATIONS

European Search Report dated Aug. 27, 1996.
Aphios Corporation, Company Bulletin, Nov. 1993.
Crystal, R.G., "Gene Therapy Strategies for Pulmonary Disease", *Am. J. Med.*, Jun. 1992, 92:6A pp. 44S–52S.
Cygnarowicz, M.L., "Design and Control of a Process to Extract β–Carotene with Supercritical Carbon Dioxide", *Biotechnol. Prog.* (1990) 6:82–91.
Debenedetti, P.G. et al., "Application of supercritical fluids for the production of sustained delivery devices", *J. Controlled Release* (1993) 24:27–44.
Debenedetti, P.G. et al., "Rapid Expansion of Supercritical Solutions (RESS): Fundamentals and Applications", *Fluid Phase Equilibria* (1993) 82:311–321.
Debenedetti, P.G. et al., "Supercritical Fluids: A New Medium for the Formation of Particles of Biomedical Interest", *Proc. Int. Symp. Control Rel. Bioact. Mater.* (1993) 20:141–142.
Donsi, G. et al., "Micronization by Means of Supercritical Fluids: Possibility of Application to Pharmaceutical Field", *Pharm. Acta Helv.* (1991) 66:170–173.

(List continued on next page.)

*Primary Examiner*—Aaron J. Lewis
*Attorney, Agent, or Firm*—Greenlee, Winner and Sullivan, P.C.

[57] ABSTRACT

Methods and apparatuses are provided for forming fine particles of a desired substance comprising dissolving said substance in a fluid such as water to form a solution and mixing the solution with a second fluid such as supercritical carbon dioxide which becomes a gas upon rapid pressure release, and with which the first fluid is at least partially immiscible, and releasing the pressure to form an air-borne dispersion or aerosol comprising particles having an average diameter between about 0.1 and about 6.5 μm.

24 Claims, 5 Drawing Sheets

U.S. PATENT DOCUMENTS

| | | | |
|---|---|---|---|
| 3,694,546 | 9/1972 | Roth et al. | 424/45 |
| 3,856,185 | 12/1974 | Riccio | 222/193 |
| 3,869,070 | 3/1975 | Schmoegner et al. | 222/635 |
| 4,066,596 | 1/1978 | Stern | 260/29 |
| 4,161,458 | 7/1979 | Kolleth | 252/305 |
| 4,215,103 | 7/1980 | Millington | 424/4 |
| 4,536,323 | 8/1985 | Stopper | 252/305 |
| 4,582,731 | 4/1986 | Smith | 427/421 |
| 4,734,227 | 3/1988 | Smith | 264/13 |
| 4,734,451 | 3/1988 | Smith | 524/493 |
| 4,790,305 | 12/1988 | Zoltan et al. | 128/200.23 |
| 4,800,903 | 1/1989 | Ray et al. | 131/273 |
| 4,814,161 | 3/1989 | Jinks et al. | 424/45 |
| 4,845,056 | 7/1989 | Yamanis | 501/12 |
| 4,892,232 | 1/1990 | Martin | 222/207 |
| 4,895,719 | 1/1990 | Radhakrishnan et al. | 424/45 |
| 4,923,720 | 5/1990 | Lee et al. | 427/422 |
| 4,963,367 | 10/1990 | Ecanow | 424/485 |
| 4,970,093 | 11/1990 | Sievers et al. | 427/38 |
| 5,002,048 | 3/1991 | Makiej, Jr. | 128/200 |
| 5,013,720 | 5/1991 | Whitsett | 514/12 |
| 5,043,280 | 8/1991 | Fischer et al. | 435/240 |
| 5,044,523 | 9/1991 | McNab | 222/207 |
| 5,056,511 | 10/1991 | Ronge | 128/200 |
| 5,115,803 | 5/1992 | Sioutas | 128/200 |
| 5,126,126 | 6/1992 | Varaprath et al. | 424/71 |
| 5,156,747 | 10/1992 | Weber et al. | 210/744 |
| 5,169,433 | 12/1992 | Lindsay et al. | 71/118 |
| 5,266,205 | 11/1993 | Fulton et al. | 210/639 |
| 5,301,664 | 4/1994 | Sievers et al. | 128/200.23 |
| 5,639,441 | 6/1997 | Sievers et al. | 424/9.3 |
| 5,707,634 | 1/1998 | Schmitt | 424/400 |
| 5,770,559 | 6/1998 | Manning et al. | 514/2 |

OTHER PUBLICATIONS

Fine, L.W and Beall, H., "Chemistry for Engineers and Scientists", Saunders College Publishing (1990), p. 288.

Foreman, W.T. et al., "Supercritical fluid chromatography with redox chemiluminescence detection", *Fresnius Z Anal. Chem.* (1988) 330:231–234.

Foreman, W.T. et al., "Supercritical Fluid Chromatography with Sulfur Chemiluminescence Detection", *J. Chromatography*, (1989) 465:23–33.

Gerrity, T.R. et al., "Calculated depostion of inhaled particles in the airway generations of normal subjects", *J. Appl. Physiol.: Respirat. Environ. Exercise Physiol.* (1979) 47(4):867–873.

Hannay, J.B. et al, "On the Solubility of Solids in Gases", *The Chemical News*, (1879) pp. 324–326.

Hickey, A.J., "Lung Depostion and Clearance of Pharmaceutical Aerosols: What Can be Learned from Inhalation Toxicology and Industrial Hygiene?", *Aerosol Science and Tech.* (1993) 18:290–304.

Ho–Mu Lin et al., "Inactivation of *Saccharomyces cerevisiae* by supercritical and Subcritical Carbon Dioxide", *Biotechnol. Prog.* (1992) 8:458–461.

Hunter, B.T. "A Different Kind of Solvent", *Consumer's Research* (1988) 71:8.

Hybertson, B.M. et al., "Pulmonary Drug Delivery of Fine Aerosol Particles From Supercritical Fluids", *J. Aerosol Medicine* (1994) 6(4):275–.

Kamihira, M. et al., "Sterilization of Microorganisms with Supercritical Carbon Dioxide", *Agric. Biol. Chem.*, (1987), 51(2):407–412.

Kebarle, P. and Tang, L., "From Ions in Solution to Ions in The Gas Phase", *Analytical Chemistry* (1993) 65:972–986.

King, M.B. et al., "Mutual Solubilities of Water with Supercritical and Liquid Carbon Dioxide", *J. of Supercritical Fluids* (1992) 5:296–302.

King, M.B. and Bott, T.R., "Introduction" to *Near Critical Solvents* (Chapman & Hall pub., London, UK) (1993) pp. 1–33.

Langer, R., "New Methods of Drug Delivery", Articles (Sep. 1990), pp. 1527–1533.

Masayuki Sato, "The Production of Essentially Uniform–Sized Liquid Droplets in Gaseous or Immiscible Liquid Media Under Applied A.C. Potential", *J. of Electrostatics*, (1984) 15:237–247.

Matson, D.W. et al., "Rapid Expansion of Supercritical Fluid Solutions: Solute Formation of Powders, Thin Films, and Fibers", *Ind. Eng. Chem. Res.* (1987) 26:2298–2306.

Mohamed, R.S. et al., "Effects of Process Conditions on Crystals Obtained from Supercritical Mixtures", *AIChE Journal* (1989) 35/2:325–328.

Mohamed, R.S. et al., "Solids Formation After the Expansion of Supercritical Mixtures", *Supercritical Fluid Science and Tech.* (1989) 355–378.

Morsy, M.A. et al., "Progress Towards Human Gene Therapy", *JAMA* (1993) 270/19:2338–2345.

Muir, D.C.F. and Verma, D.K., "Occupational and environmental aerosols. Characterization and clinical relevance", *Aerosols in Medicine. Principles, Diagnosis and Therapy*, Newhous, M.T. and Dolovich, M.B. (eds) (1985), pp. 313–332.

Musser, S.M. and Callery, P.S., "Supercritical Fluid Chromatography/Chemical Ionization/Mass Spectrometry of Some Anticancer Drugs in a Termospray Ion Source", *Biomedical and Environ. Mass Spectrometry* (1990) 19:348–352.

Newman, S.P. et al., "Therapeutic aerosols 1—Physical and practical considerations", *Thorax* (1983) 38:881–886.

Newman, S.P., "Aerosol Deposition Considerations in Inhalation Therapy", *Chest* (1985) 88:152S–160S.

Newman, S.P. et al., "Aerosols in therapy", *Aerosols in Medicine. Principles, Diagnosis and Therapy*, Moren, F., Newhouse, M.T. and Dolovich, M.B. (eds) (1985), pp. 289–312.

Palmieri, M.D., "An Introduction to Supercritical Fluid Chromatography", *J.Chem.Ed.* (1988), 65:A254–259.

Rossaint, R. et al., "Inhaled Nitric Oxide for the Adult Respiratory Distress Syndrome", *N.E. Jrnl. Med.* (1993) 328:6:399–405.

Rudolf, R. and Wagner, P.E., "Experiments on Binary Condensational Particle Growth for the Nearly Immiscible System Water—n–Nonane", *J. Aerosol. Sci.*, (1992) 23:S117–S120.

Sadoun, Fr. et al., "Packed–column supercritical fluid chromatography coupled with electrospray ionization mass spectrometry", *J. Chromatography* (1993) 647:351–359.

Sang–Do Yeo et al., "Formation of Microparticulate Protein Powders Using a Supercritical Fluid Antisolvent", *Biotechnology and Bioengineering*, (1993) 41:341–346.

Schelkle, M. et al., "Droplet Formation Simulated with an Immiscible Lattice Gas Model", *J. Aerosol Sci.* (1992) 23:S245–S248.

Swift, David L., "Aerosol characterization and generation", *Aerosols in Medicine. Principles, Diagnosis and Therapy*, Moren, F., Newhouse, M.T. and Dolovich, M.B. (eds) (1985), pp. 53–76.

Tom, J.W. and Debenedetti, P.G., "Particle Formation with Supercritical Fluids—A Review", *J. Aerosol Sci.* (1991) 22:555–584.

Tom, J.W. et al., "Applications of Supercritical Fluids in the Controlled Release of Drugs", *Supercritical Fluid Engineering Sci.*, (1993), pp. 238–257.

Tom, J.W. and Debenedetti, P.G., "Formation of Bioerodible Polymeric Microspheres and Microparticles by Rapid Expansion of Supercritical Solutions", *Biotechnol. Prog.* (1991) 7:403–411.

Tom, J.W. and Debenedetti, P.G., "Precipitation of Poly(Hydroxy Acids) and Coprecipitation of Polymer/Drug Particles by Rapid Expansion of Supercritical Solutions", 104–105.

Washington, N. et al., "Pulmonary Drug Delivery", *Physiological Pharmaceutics—Biological Barriers to Drug Absorption*, Rubinstein, M.H. (ed.) (1989) pp. 155–178.

Wong, J.M. and Johnston, K.P., "Solubilization of Biomolecules in Carbon Dioxide Based Supercritical Fluids", *Biotechnology Progress* (1986) 2/1:29–39.

METHODS AND APPARATUS FOR FINE PARTICLE FORMATION

CROSS REFERENCE TO RELATED PATENTS

This application is a divisional of U.S. Ser. No. 08/224,764 filed Apr. 8, 1994, now U.S. Pat. No. 5,639,441, which is a continuation-in-part of U.S. Ser. No. 07/846,331 filed Mar. 6, 1992, now U.S. Pat. No. 5,301,664, both of which are incorporated herein by reference.

FIELD OF THE INVENTION

The present invention relates to methods and apparatuses using supercritical fluid mixtures for forming fine particles for drug delivery, mass spectrometry, powder and film formation and other applications.

BACKGROUND OF THE INVENTION

Aerosols and vapors have a variety of medicinal and industrial uses. An aerosol is a two-phase system consisting of a gaseous continuous phase and a discontinuous phase of individual particles. Vapors are molecularly dispersed and are a single gaseous phase. The individual particles in an aerosol can be solids or liquids (Swift, D. L. (1985), "Aerosol characterization and generation," in Aerosols in Medicine Principles, Diagnosis and Therapy (Moren, F. et al. eds) 53–75).

Liquids under pressure have been used to purify and mix products to a desired final form. U.S. Pat. No. 5,056,511 to Ronge for "Method and Apparatus for Compressing, Atomizing and Spraying Liquid Substances," issued Oct. 15, 1991, discloses atomizers for creating small droplets of liquids, such as peanut oil in which vitamins A and E are solubilized, involving compression of the liquid at a pressure of 300 to 800×10$^5$ Pa and the sudden release of pressure to cause an explosive spray. U.S. Pat. No. 5,169,433 to Lindsay et al. issued Dec. 8, 1992 for "Method of Preparing Mixtures of Active Ingredients and Excipients Using Liquid Carbon Dioxide" discloses the use of liquid (not supercritical) carbon dioxide under pressure to solubilize active ingredients and excipients, and slow conversion of the liquid carbon dioxide to the gaseous phase to form a product which can be easily solubilized or dispersed in water.

Supercritical fluids have been used in the production of aerosols for precipitation of fine solid particles. The phenomenon was observed and documented as early as 1879 by Hannay, J. B. and Hogarth, J., "On the Solubility of Solids in Gases," Proc. Roy. Soc. London 1879 A29, 324, who described the precipitation of solids from supercritical fluids: "When the solid is precipitated by suddenly reducing the pressure, it is crystalline, and may be brought down as a 'snow' in the gas, or on the glass as a 'frost' . . . ."

This phenomenon has been exploited in processes for producing fine particles, however, its use has been limited to substances which are soluble in the supercritical fluid.

Mohamed, R. S., et al. (1988), "Solids Formation After the Expansion of Supercritical Mixtures," in Supercritical Fluid Science and Technology, Johnston, K. P. and Penninger, J. M. L., eds., describes the solution of the solids naphthalene and lovastatin in supercritical carbon dioxide and sudden reduction of pressure to achieve fine particles of the solute. The sudden reduction in pressure reduces the solvent power of the supercritical fluid, causing precipitation of the solute as fine particles.

Tom, J. W. and Debenedetti, P. B. (1991), "Particle Formation with Supercritical Fluids—a Review," J. Aerosol. Sci. 22:555–584, discusses rapid expansion of supercritical solutions (RESS) techniques and their applications to inorganic, organic, pharmaceutical and polymeric materials. The RESS technique is useful to comminute shock-sensitive solids, to produce intimate mixtures of amorphous materials, to form polymeric microspheres and deposit thin films. Critical properties of common RESS solvents are provided. The solvents include carbon dioxide, propane, n-pentane, propylene, ethanol, and water. In all cases the RESS process requires dissolving of at least one solid in the supercritical fluid.

Smith U.S. Pat. No. 4,582,731 for "Supercritical Fluid Molecular Spray Film Deposition and Powder Formation," issued Apr. 15, 1986, and Smith U.S. Pat. No. 4,734,451 for "Supercritical Fluid Molecular Spray Thin Films and Fine Powders," both of which are incorporated herein by reference, describes a typical RESS process involving rapidly releasing the pressure of a supercritical solution of a solid solute to form a film of the solute on a substrate, or to form a fine powder of the solute.

Sievers et al. U.S. Pat. No. 4,970,093 for "Chemical Deposition Methods Using Supercritical Fluid Solutions," issued Nov. 13, 1990, incorporated herein by reference, discloses a process similar to the RESS process for depositing a film on a substrate by rapidly releasing the pressure of a supercritical reaction mixture to form a vapor or aerosol which deposits a film of the desired material on a substrate. Alternatively, the supercritical fluid contains a dissolved first reagent which is contacted with a gas containing a second reagent which reacts with the first reagent to form particles of the desired material deposited as a film on the substrate.

Sievers, et al. PCT Publication WO 9317665 published Sep. 16, 1993, corresponding to the parent application hereof, discloses the use of nebulizers utilizing medicaments dissolved in supercritical fluids to deliver physiologically active substances to a patient, preferably to lung tissues of the patient. The supercritical fluid process provides particles of the desired size range for administration to the patient's lungs (less than about 6.5 $\mu$m). The process is limited to solutes which will dissolve in the supercritical fluid or the supercritical fluid and cosolvents.

The use of supercritical co-solvents, e.g., carbon dioxide and nitrous oxide, to dissolve poorly soluble active principles is described in Donsi, G. and Reverchon, E. (1991), "Micronization by Means of Supercritical Fluids: Possibility of Application to Pharmaceutical Field," Pharm. Acta Helv. 66:170–173.

A modification of the RESS process is described in PCT Publication WO 90/03782 of The Upjohn Company for "Finely Divided Solid Crystalline Powders via Precipitation Into an Anti-Solvent" which involves dissolving a desired solid in a supercritical fluid and adding an anti-solvent which is miscible with the supercritical fluid but not with the solute in order to precipitate the solute. Such an anti-solvent process, referred to as the "gas anti-solvent (GAS) precipitation process is also discussed in Debenedetti, P. G., et al. (1993), "Application of supercritical fluids for the production of sustained delivery devices," J. Controlled Release 24:27–44. The GAS process is also discussed with respect to production of insulin powder in Yeo, S -D, et al. (1993), "Formation of Microparticulate Protein Powders Using a Supercritical Fluid Antisolvent," Biotechnology and Bioengineering 41:341–346. Again, the usefulness of the process is limited to the precipitation of solutes which may be dissolved in the supercritical fluid.

None of the foregoing literature discloses or suggests the use of mixtures of supercritical fluids with immiscible liquids to process desired substances or form aerosols or vapors.

U.S. Pat. No. 5,156,747 to Weber et al. for "Separation of Liquids with Different Boiling Points with Nebulizing Chamber," issued October 20, 1992, discloses the use of a heated gas and nebulization to separate liquids having high boiling points from immiscible liquids having lower boiling points. The use of supercritical temperatures and pressures is not disclosed.

A method for forming fine particles of substances which do not readily go into solution in supercritical or pressurized fluids is not available in the art, and is an object of this invention.

Supercritical fluid processes, as discussed above, have been employed in forming fine particles for industrial and medicinal uses. In addition, supercritical fluids have been used in supercritical chromatography. See, e.g., Foreman, W. T., et al. (1989), "Supercritical fluid chromatography with sulfur chemiluminescence detection," J. Chromatogr. 465:23–33, Foreman, W. T., et al. (1988), "Supercritical fluid chromatography with redox chemiluminescence detection," Fresenius' Z. Anal. Chem. 330:231–234, and Sadoun, F., et al. (1993), "Packed-column supercritical fluid chromatography coupled with electrospray ionization mass spectrometry," J. Chromatogr. 647:351–359. These methods require a single phase fluid for chromatography rather than a two-phase fluid or immiscible mixture.

Although supercritical fluid chromatography has been coupled to various types of detectors, the methods and apparatus of this invention involving the use of immiscible mixtures of supercritical fluids with other nongaseous fluids to form fine particles to facilitate analysis by means of magnetic resonance imaging, optical emission spectroscopy, atomic absorption spectrometry, electrospray ionization mass spectrometry, and the like, do not appear to be reported in the literature.

Substances such as large molecular weight hydrophilic proteins are difficult to characterize using standard mass spectrometric techniques such as electrospray ionization mass spectrometry, because of their low solubility in the organic solvents used in such processes. The ability to use aqueous solutions of such proteins in mass spectrographic methods is a further object of this invention.

SUMMARY OF THE INVENTION

It is an object of this invention to increase the range of substances which can be delivered as fine particles by rapid pressure reduction on a carrier fluid. It is also an object of this invention to increase the range of substances which can be formed into fine particles by supercritical fluid precipitation. At present only substances which are soluble in pressurized or supercritical fluid, with or without the aid of cosolvents and surfactants, are amenable to such processes. This invention provides a process for forming fine particles of substances which are soluble in fluids, preferably nongaseous fluids, immiscible with the pressurized or supercritical fluid. This expands the range of substances which can be delivered and eliminates the need for co-solvents and surfactants.

The processes of this invention are particularly noteworthy for substances which are significantly soluble only in water, because the critical temperature of water is 3740 C, and transforming aqueous solutions into the supercritical state decomposes most organic compounds. Therefore, it was advantageous to discover a new method for forming fine aerosol droplets of aqueous solutions.

In the processes of this invention, fine aerosols comprising the desired substance are formed by mixing a nongaseous pressurized or supercritical fluid with the desired substance which is present in a solution, dispersion, suspension, micellar system or emulsion in another nongaseous fluid to form an immiscible mixture. That is, the pressurized or supercritical fluid is at least partially immiscible with the carrier fluid for the desired substance. This immiscible mixture is preferably an intimate mixture, by which is meant a suspension, emulsion, micellar system, or dispersion of one fluid in the other. The immiscible mixture need not be a stable emulsion. Preferably, the two mutually immiscible phases of the immiscible mixture are not physically entirely separated from each other, but are mixed such that the phase present in the lowest volume forms droplets having a size from submillimeter to at most about 5 mm in diameter in the major phase.

In targeting drugs to various tissues of the lungs, it is important to provide particle sizes within the appropriate size range. See, e.g., Newman, S.P. et al. (1983), "Therapeutic aerosols 1—Physical and practical considerations," Thorax 38:881–886; Newman, S. P. (1985), "Aerosol Deposition Considerations in Inhalation Therapy," Chest 88:152S–160S; and Gerrity, T. R. et al. (1979), "Calculated deposition of inhaled particles in the airway generations of normal subjects," J. Appl. Physiol. 47:867–873. From the literature, it is known that only particles with diameters smaller than about 6.5 $\mu$m, preferably smaller than about 5.0 $\mu$m, will reach the alveoli and be deposited there. By the process of this invention particles of the desired size range may be produced, i.e. less than about 6.5 $\mu$m.

This invention provides a method and apparatus for the delivery of aerosol particles both as solids and as liquid, e.g., aqueous, droplets that are smaller in diameter than usually formed by existing technologies, for treatment or diagnosis of disease in humans, animals or plants. The methods of this invention may also be used to provide powders and film coatings for industrial use, for cloud seeding to increase precipitation, for delivery of fine droplets of an aqueous solution to the ionization chamber of an electrospray mass spectrometer or other detection device, and for other purposes known to the art in which fine particle generation is required.

The method provided herein for forming fine particles of a substance comprises:

(a) substantially dissolving or suspending said substance in a first nongaseous fluid to form a first solution or suspension;

(b) mixing said first solution or suspension with a second nongaseous fluid to form a composition comprising:

(1) said substance;
(2) an immiscible mixture of said first and second nongaseous fluids;
(c) rapidly reducing the pressure on said composition whereby at least one of said nongaseous fluids forms a gas, and whereby a gas-borne dispersion of said fine particles of said substance is formed.

Particles having an average diameter from about 0.1 μm to less than or equal to about 6.5 μm are formed, preferably less than or equal to about 5 μm, and most preferably between about 1 μm and about 5 μm. The term "particle" as used herein refers to both solid particles and liquid droplets.

The term "suspension" as used herein includes dispersions, emulsions and micellar systems. The term "substantially dissolving" as used herein means that the substance is dissolved or so intimately dispersed in the first fluid that a uniform fluid results in which the substance is suspended in the form of particles less than about 6.5 μm. The term "dissolving" means the formation of a true solution. A preferable class of desired substances have at least about 0.1% solubility in water, methanol, ethanol, or dimethylsulfoxide.

The substance to be dissolved, substantially dissolved, or suspended in the first solution may be a medicament or physiologically active composition, e.g., an antimicrobial agent, virus, antiviral agent, antifungal pharmaceutical, antibiotic, nucleotide, DNA, antisense cDNA, RNA, amino acid, peptide, protein, enzyme, immune suppressant, thrombolytic, anticoagulant, central nervous system stimulant, decongestant, diuretic vasodilator, antipsychotic, neurotransmitter, sedative, hormone, anesthetic, surfactant, analgesic, anticancer agent, antiinflammatory, antioxidant, antihistamine, vitamin, mineral, or other physiologically active material known to the art. The substance must be present in a physiologically effective amount in the aerosol generated by the process of this invention.

The fine particles may also include delivery agents such as liposomes, water soluble polymers such as polylactic acid and polyglycolic acid, controlled-delivery coatings, surfactants, viruses, dimethylsulfoxide, nitric oxide, and other delivery agents known to the art.

Pulmonary administration of fine particles is useful for diagnosis; e.g., MRI contrast agents or radio-labelled particles may be administered. Such fine particles administered to the lungs are useful for diagnosis of pulmonary function abnormalities, structural abnormalities, blockages, tumors and mismatches in ventilation and perfusion. The fine particles may include $Na_2Fe(DTPA)$, $Na_2Cr(DTPA)$, $Na_2Gd(DTPA)$, dimedone salts of gadolinium(III) contrast agents, radioactive rhenium- or phosphorus-containing salts, TEMPO spin-label agents and other aids to contrasting.

The substance to be formed into fine particles may be an agricultural chemical, commercial chemical, fine chemical, food item, nutrient, pesticide, photographic chemical, dye, explosive, paint, polymer, cosmetic, protective agent, metal coating precursor, or other industrial substance whose final form is a deposited film, fine particle dispersion or powder.

The substance to be formed into fine particles may be a cloud seeding agent, a nucleation agent, an obscurant, or a catalyst such as silver iodide, *Erwinia herbicola, Pseudomonas syrinae,* colloidal silver, titanium dioxide, and other such agents known to the art.

Further, the dissolved substance may be any molecule or portion of a molecule or ion that is desirable to detect by means of ionization, chromatographic or spectroscopic means.

The first fluid may be any solvent, polar or nonpolar, capable of dissolving the said substance either at standard temperature and pressure or at elevated temperatures and/or pressures. Co-solvents and surfactants may also be present in either fluid. The second fluid may be any fluid which is insoluble or only partially soluble in the first fluid.

When the first fluid containing the dissolved substance and the second fluid are mixed, the mixture may be comprised partially of a solution of the first and second fluids to the extent they are soluble in each other. The mixture will also be a two-phase mixture in that it will comprise an immiscible mixture of the first and second fluids. Preferably at equilibrium, the ratio of the fluid present at lesser volume in the mixture to the fluid present at greater volume will be at least about 1:1000. The solubility of the first fluid in the second fluid may be negligible. Either or both fluids may be present in quantities in excess of that which will dissolve in the other.

In a preferred embodiment, the mixture comprises a solution of the first fluid and the second fluid such that when the pressure is rapidly reduced, at least one of said fluids forms a gas. The pressure release should be rapid enough that the gas formation is explosive, causing the formation of fine particles comprising the dissolved substance. The fine particles may be solid or liquid, and may comprise the dissolved substance in solution or suspension.

In a preferred embodiment, one of the fluids, preferably the second fluid, is a supercritical fluid and the pressure is rapidly released, preferably from above the supercritical pressure to ambient pressure. Within the context of the present invention, reference to the supercritical fluid solution indicates that the solution is above its critical pressure and temperature or is sufficiently close to the critical pressure and temperature to cause the formation of a gas-borne dispersion of solute particles of an average size of from about 0.1 μm to about 6.5 μm in diameter upon rapid expansion of the mixture into a subcritical, preferably ambient region.

A number of fluids suitable for use as supercritical fluids are known to the art, including carbon dioxide, sulfur hexafluoride, chlorof luorocarbons, fluorocarbons, nitrous oxide, xenon, propane, n-pentane, ethanol, nitrogen, water, other fluids known to the art, and mixtures thereof. The supercritical fluid is preferably carbon dioxide or mixtures of carbon dioxide with another gas such as fluoroform or ethanol. Carbon dioxide has a critical temperature of 31.3 degrees C and a critical pressure of 72.9 atmospheres (1072 psi), low chemical reactivity, physiological safety, and relatively low cost. Another preferred supercritical fluid is nitrogen.

When one of the fluids is a supercritical fluid, the other may be another supercritical fluid or a liquid. Preferably the first fluid comprises water, ethanol, methanol or dimethyl sulfoxide.

The fluids may contain surfactants, co-solvents, antisolvents, and other components. They may be mixtures of several different mutually soluble components such as methanol and water.

In one preferred embodiment, the first fluid comprises water, and preferably is water in which the desired substance is dissolved, and the second fluid is a supercritical fluid such as carbon dioxide present in sufficient quantity to be immiscible with water.

In another embodiment, the first fluid comprises water, and preferably is water in which the desired substance is dissolved, and the second is nitrogen maintained above its critical temperature and pressure.

In one embodiment, the supercritical fluid solution may be formed by mixing the fluid to be made supercritical and the solution or suspension of the desired substance, pressurizing the resulting mixture above the critical pressure of the fluid to be made supercritical, and heating the resulting mixture above the critical temperature of the fluid to make at least one fluid supercritical.

Alternatively, the supercritical fluid may be formed by pressurizing the fluid above its critical pressure, mixing it with the solution or suspension of the desired substance, and heating the mixture above the critical temperature.

Intimate mixtures, e.g., dispersions, emulsions or micellar systems, of the fluids with and without the aid of surfactants may be formed in batch processes or on-line with mixing of concurrent stream flows, preferably with low dead volume devices as hereinafter described.

The mixture comprising the immiscible fluids is passed into a region of lower pressure such that decompression occurs rapidly, i.e., within about $10^{-6}$ seconds, causing at least one of the fluids to enter the gaseous phase and precipitate a dispersion of fine particles comprising the dissolved substance.

Subcritical fluids may be used in the process of this invention. For example a mixture of an aqueous solution and subcritical carbon dioxide may be used. In such a case, the solubility of one fluid in the other should be measurably changed by changes in pressure such that rapid removal of pressure from the system will cause the evolution of dissolved gas to facilitate break-up of the droplets and particles.

Delivery of physiologically active fine aerosol particles via the respiratory system is receiving increasing attention by scientists and the public, especially for pharmaceuticals which require rapid absorption and those that are destroyed in the stomach after oral application.

In a preferred embodiment in which the dissolved substance is a physiologically active agent, the method includes in vivo or in vitro deposition of a therapeutically effective amount of fine particles of the substance on tissues, preferably respiratory tissues, of a patient. The particles may also induce physiological responses following uptake in the nasal or other mucosa. Antibiotics, vitamins, minerals, analgesics, antihistamines, hormones, antimicrobials, antioxidants, anticancer agents, agents useful in gene therapy, and other medicaments known to the art are useful in the processes of this invention. These medicaments may be administered in vivo directly by deposit of the aerosol on the tissue or organ to be treated, such as the lungs, and the like, or alternatively, the fine particles produced in the process of this invention may be delivered in vitro by dissolving or suspending in a suitable physiological carrier for injection, oral administration, or administration by other methods known to the art. For example, the particles may be administered into harvested tissue such as liver tissue in vitro, and the treated tissue returned to the body.

Suitable physiologically active agents include without limitation: LEUSTATIN™ (cladribine) useful in the treatment of hairy cell leukemia, insulin useful in the treatment of diabetes, erythropoietin useful in stimulating red blood cell production, RISPERDAL™ (resperidone) useful in the treatment of schizophrenia, the psychoactive drugs serotonin and dopamine and their antagonists, amphotericin B, antifungus agents, Livostin (levocabastine hydrochloride), useful in the treatment of allergic conjunctivitis, SURVANTA™, Exosurf and other surfactants useful for treatment of lung conditions such as surfactant deficiencies.

The physiologically active substances useful in this invention also include without limitation, acetaminophen, acetylcysteine, aminosalicylate sodium, ascorbic acid, aspirin, caffeine, calcium gluconate, citric acid, cyanocobalamin, ferrous gluconate, ferrous sulfate, heparin sodium, hydrocortisone sodium phosphate, insulin, magnesium sulfate, methylene blue, methylparaben, methylprednisolone sodium, niacin, oxtriphylline, oxymorphone hydrochloride, oxyphencyclimine hydrochloride, paraldehyde, paromomycin sulfate, pentazocine hydrochloride, phenindamine tartrate, phenol, polyethylene glycol 1540, potassium permanganate, prednisolone, sodium phosphate, resorcinol, silver nitrate, sodium bicarbonate, sodium borate, sodium nitrite, sodium thiosulfate, sorbitol, stearic acid, sulfisoxazole diolamine, tetracycline hydrochloride, tetracycline phosphate complex, theophylline, sodium glycinate, thiamine hydrochloride, thiamine mononitrate, thymol, trimeprazine tartrate, urea, vanillin, xylometazoline hydrochloride, and zinc acetate.

Examples of antibiotics that may be employed as the physiologically active solute in the methods of the present invention include, but are not limited to, tetracycline, chloramphenicol, aminoglycosides, for example, tobramycin, beta-lactams, for example, ampicillin, cephalosporins, erythromycin and derivatives thereof, clindamycin, and the like. Suitable anti-viral agents include acyclovir, ribavirin, ganciclovir and foscarnet. Anti-inflammatory drugs include but are not limited to aqueous solutions of naproxen sodium. Suitable antineoplastic agents include but are not limited to etoposide, taxol and cisplatin. Antihistamines include but are not limited to diphenhydramine and ranitidine. Hormones include but are not limited to insulin, testosterone and estrogen. Antiasthma drugs include but are not limited to PROVENTIL™, an aqueous solution of albuterol sulfate and benzalkonium chloride. These specific physiologically active compounds are only examples of the numerous active compounds which may be employed in the methods of the present invention.

In a preferred embodiment of the present method, the physiologically active solute is a drug for the treatment of a pulmonary disorder. In this regard, preferred active compounds are selected from the group consisting of rhDNAse, cromolyn sodium, and terbutaline sulfate.

Other useful bioactive agents include substances useful in gene therapy, either administered through the blood or liver, or deposited directly on the tissue to be affected. Such agents include without limitation: glucocerbrosidase, ornithine transcarbamylase, cystic fibrosis transmembrane regulator, hypoxanthine guanine phosphoribosyl transferase, low-density lipoprotein receptor (with a harmless virus to facilitate transport), cell adhesion molecules, adenosine deaminase, tumor suppression genes and other genes known to the art for gene therapy, including the retinoblastoma tumor-suppressor gene, and p53. Other fine particles that can be delivered include liposome-based antisense cDNA, chromosomes, DNA, nucleosidase, proteins, fibroblasts, retroviral vectors, and other biological materials.

Polylysine, a ligand-mediated DNA conjugate, lipofection, a cationic lipid used in gene therapy, asialoglycoprotein, fusogenic peptides of the influenza HA protein, adenovirus and other transport viruses can be used to insert genetic materials into cells.

Another benefit of practicing the new method of pressurizing an aqueous solution in intimate contact with, or an emulsion in, a supercritical fluid such as carbon dioxide, and rapidly depressurizing the mixture, is illustrated by the following process useful in gene therapy.

In this application, the principal benefit is producing genetically-modified biological materials which are fine particles, such as cells. The cells to be altered are suspended in an aqueous solution containing foreign genetic material, e.g., DNA to be inserted into the cells. This aqueous mixture is pressurized and mixed intimately with supercritical carbon dioxide in a flowing emulsion stream. The pressurized emulsion is then decompressed much more rapidly than it was compressed, and forms an aerosol as in the other applications. Control of the rates and magnitudes of pressurization and depressurization are more critical in handling living cells than in applying the method to non-living constituents of emulsions. If molecules of carbon dioxide from the supercritical fluid part of the emulsion diffuse slowly over several minutes through the extra-cellular water and across the cell walls while under pressure, the nucleus of the cell becomes momentarily supersaturated with carbon dioxide. If the pressure is suddenly released partially or totally, to atmospheric pressure, the gas in the nucleus will stretch, or form fissures in, cell walls and nuclear membranes, thereby allowing leakage of the foreign DNA into the nucleus where genetic alterations may result. Cell wall repair and replication of the modified cells follows if the aerosols and fluids are collected in aqueous solutions with appropriate cell growth nutrients.

It should be emphasized that this process differs from methods aimed at sterilizing by killing bacteria, e.g., as reported in Lin, H. M., et al. (1992), "Inactivation of *Saccharomyces cerevisia* by Supercritical and Subcritical Carbon Dioxide," Biotechnol. Prog. 8:458–461, and Kamihira, M., et al. (1987), "Sterilization of Microorganisms with Supercritical Carbon Dioxide," Agric. Biol. Chem. 51:407–412. Conditions in the present method are chosen so as not to kill the cells. The purpose is to use mild enough conditions to insure survival of the cells rather than destroying them by catastrophic massive rupture of cell walls. This can be accomplished by depressurizing at a rate faster than the pressurization, but slower than that causing lethal blow-outs of cell walls. Preferably, the pressurization takes place over minutes, while depressurization takes place over milliseconds, and can occur in multiple steps. It may be advantageous to cycle cells more than once to pressures between 15 psig and up to from approximately 1,100 to 10,000 psig. The addition of about 1% of co-additives such as liposomes, surfactants, toluene or dimethylsulfoxide to the suspension may make the cell walls more permeable.

The aerosol or gas-borne dispersion may be mixed with oxygen or humidified air, synthetic air or other gases or diluents. In a preferred embodiment, nitric oxide may be added to the mixture, preferably in an amount of at least about 1.0 ppm up to about 50% of the mixture, but not so high as to cause toxic effects, by incorporation into the supercritical fluid, to facilitate relaxation of smooth muscle with subsequent dilation of airways and blood vessels, and uptake in living systems or to simultaneously treat for adult respiratory distress syndrome (ARDS). Rossaint, R., et al. (1993), "Inhaled Nitric Oxide for the Adult Respiratory Distress Syndrome," N. Engl. J. Med. 238:399–405, has described the administration by inhalation of 18 to 36 ppm of nitric oxide in air for treatment of patients with ARDS. Many other examples of therapeutic use of nitric oxide and its precursors are known to the art.

It is sometimes desirable to dilute the aerosol formed by rapid expansion of supercritical fluids, such as with a stream of air or nitrogen when the aerosol is being chronically or continuously administered to the lungs in order to prevent hypercarbia, and in order to provide an air-like mixture for breathing.

In a further embodiment involving use of the process for industrial coatings, the dissolved substance may be a resin, a polymer, a metal coating precursor (e.g., $H_2Fe(DTPA)$), a metal oxide precursor (e.g., $Cr(NO_3).9H_2O$), precursors to a glass (e.g., silicic acid) or a water-based emulsion paint.

MRI spin relaxation agents such as disodium diethylenetriaminepentaacetato-iron(III), ($Na_2Fe(DTPA)$), $Na_2Gd$ (DTPA), or $Na_2Cr(DTPA)$ may also serve as the dissolved substances in the process of this invention for use in investigating maladies of the lung by nuclear magnetic resonance spectroscopy.

The mixture may also be diluted with hot air, nitrogen or other gases as an aid to drying the aerosol. Air or oxygen can be added to the emulsions or solutions, or the aerosols formed therefrom to aid in forming coatings in industrial processes, and the aerosol can also be heated to facilitate reactions to form coatings or fine particles.

The process of this invention may also be used in the source regions of electrospray mass spectrometers or other detectors to provide a new chemical profile of the substance being tested. Different mass spectra are obtained from those obtained using conventional nebulization without a supercritical fluid emulsion.

The nebulization technique of this invention may be used for absorption spectroscopy, atomic emission spectroscopy, inductively coupled plasma, optical emission spectroscopy, and for other plasma applications, flame ionization detection, or gas chromatography detection, and for other mass spectrographic applications.

This invention also provides a device for making fine particles of a substance having an average diameter of less than about 6.5 $\mu$m comprising:

(a) a first chamber containing a first nongaseous fluid, preferably a supercritical fluid;

(b) a second chamber containing a solution or suspension of said substance in a second nongaseous fluid, preferably water, at least partially immiscible with said supercritical fluid;

(c) a mixing chamber for mixing said solution and first fluid connected to said first and second chambers by conduits;

(d) flow control means connected to the conduit between the first chamber and the mixing chamber for passing said first fluid into said mixing chamber;

(e) flow control means connected to the conduit between the second chamber and the mixing chamber for passing said solution or suspension into said mixing chamber so as to provide a composition within said mixing chamber comprising an immiscible mixture of said fluids;

(f) means for rapidly expanding the composition in the mixing chamber into a region in which the temperature and pressure are below the critical temperature and pressure of the supercritical fluid to form a dispersion of fine particles of said substance.

The device may also comprise heating means for maintaining a supercritical temperature in the first chamber and/or the mixing chamber. The flow control means may include a combination of valves and restrictors, and if necessary, pumping means for controlling the flow of the fluid and solution. Means for contacting the substance with the solvent to form the said solution may also be provided as part of the apparatus.

Another embodiment of this invention involves the use of a single canister containing the pressured immiscible mixture. This device for making fine particles of a substance comprises:

(a) a pressurized chamber containing at least two immiscible nongaseous fluids, and also comprising a suspension or solution of said substance;

(b) a pressure-resistant septum covering an orifice in said chamber;

(c) a nozzle having a piercing end adjacent to said septum which operates to pierce said septum during use, said nozzle having a conduit therethrough;

(d) puncture forcing means for moving the piercing end of said nozzle through said septum whereby during use an intimate mixture of said immiscible nongaseous fluids expands under pressure into said conduit and thence into the space surrounding said nozzle forming an aerosol comprising fine particles of said substance having an average diameter of less than about 6.5 $\mu$m.

The apparatuses may also include means for diluting the aerosol with air or oxygen and administering the gas-borne dispersion of fine particles to a target human or animal, such as a mouthpiece, face mask, tube, or the like.

Apparatuses suitable for forming industrial coatings or particles may also comprise means for heating the aerosol or irradiating it to induce chemical reactions to occur at or near surfaces to form substances with different compositions than the starting materials.

An apparatus serving as the source for mass spectroscopic detection comprises: means (such as two pumps) for preparing and pressurizing in a low-dead-volume mixing tee an intimate mixture of a supercritical fluid with an aqueous solution of the analyte to be nebulized, and a pressure restrictor orifice (hollow needle) made of an electrically conductive material such as stainless steel. Preferably the supercritical fluid is carbon dioxide or nitrogen, both of which can partially dissolve in the aqueous solution to facilitate droplet formation when the pressure is rapidly reduced.

The methods and apparatuses of this invention produce gas-borne dispersions of solids or liquids preferably having a particle size between about 0.1 and about 6.5 $\mu$m. These compositions, termed aerosols herein, comprise gases accompanying the solid or liquid fine particles, and may comprise other components including up to about 50% nitric oxide, preferably in compositions comprising medicaments or diagnostic agents for respiratory disease.

DETAILED DESCRIPTION OF THE PREFERRED EMBODIMENTS

Figure 1:
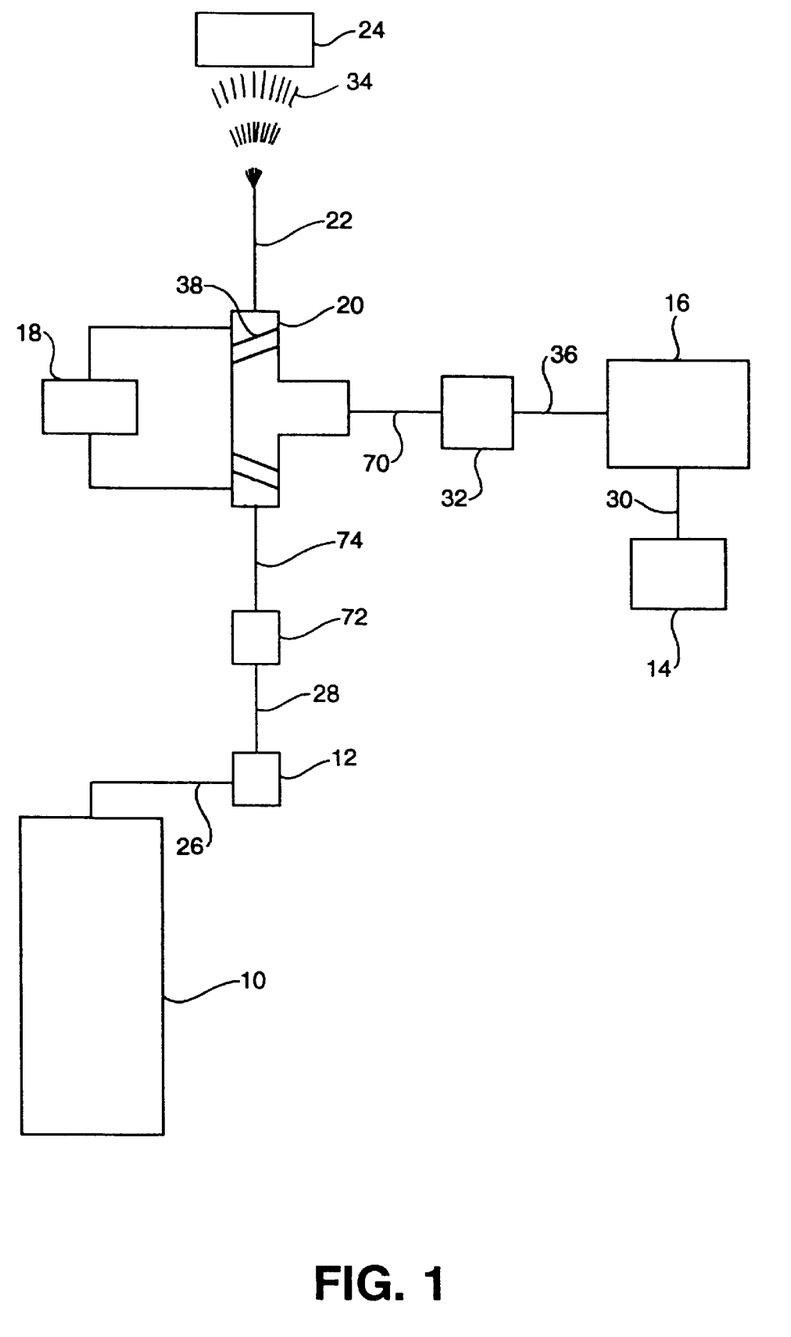
FIG. 1 is a diagram illustrating the flow of supercritical fluid and immiscible fluids to form small particles.

A preferred embodiment of the present invention is shown in FIG. 1 illustrating the flow of fluids and solutions in the method of this invention. A carbon dioxide reservoir 10 containing liquid carbon dioxide is connected with supercritical carbon dioxide pump 12 via conduit 26. Supercritical carbon dioxide pump 12 is connected to mixing tee 20 by means of conduit 28, needle valve 72 and conduit 74, through which the carbon dioxide is pumped under conditions at which it becomes a supercritical fluid when it reaches the heated mixing tee 20. Reservoir for aqueous solution 14 containing a dissolved or suspended substance is connected via conduit 30 to solution pump 16, preferably a high pressure liquid chromatography (HPLC) pump, which is connected via conduit 36, needle valve 32 and conduit 70 to mixing tee 20. Needle valves 32 and 72 are flow control valves to control the rate of flow of supercritical fluid and aqueous solution to assure that an immiscible mixture is formed in mixing tee 20. The mixing tee preferably has a low dead volume, e.g. less than about 10 $\mu$l so that an intimate mixture of the supercritical carbon dioxide and the aqueous solution may be formed therein. Mixing tee 20 is equipped with a heater 18 equipped with heating coils 38 to maintain supercritical temperature therein. The mixing tee 20 is also equipped with a restrictor capillary 22 to maintain back-pressure in mixing tee 20. Upon passage of the intimate mixture from the mixing tee 20 through the small diameter capillary restrictor 22, sudden release of the pressure at the exit of the orifice of restrictor capillary 22 occurs and an aerosol comprising gas-borne fine particles of the dissolved substance and aqueous solution 34 is formed. The particles are collected, further treated, or diluted with air and conducted into drug delivery means or collector 24. The drug delivery means may be a face mask or mouthpiece for particles to be inhaled, a collector for collecting or solubilizing the particles for injection or other use; or in the experimental model used in the Examples hereof, the apparatus includes a collector for measuring particle sizes by laser diffraction of collected aerosols.

In operation, the liquid carbon dioxide is pumped by means of supercritical carbon dioxide pump 12 from carbon dioxide reservoir 10 via conduit 26 through pump 12 and via conduit 28, needle valve 72 and conduit 74 to the low-volume (0.2 to 10 $\mu$l) mixing tee 20 where it becomes a supercritical fluid if it is not already. The aqueous solution or suspension containing active substance(s) is pumped from reservoir for aqueous solution 14 through conduit 30 by means of solution pump 16 to mixing tee 20 by means of conduit 36, needle valve 32 and conduit 70. Heater 18, including heating coils 38, maintains the temperature in mixing tee 20 above the critical temperature of the carbon dioxide. Alternatively, or additionally, capillary restrictor 22 may be heated. The two fluid flow rates are established by adjusting the two independent valves 32 and 72, which are preferably needle valves. Flow rates can also be controlled by altering pumping conditions. The immiscible mixture in mixing tee 20 expands downstream and forms aerosol 34 comprising fine particles of the substance dissolved or suspended in the aqueous solution. The particles are collected in collector 24 and a portion may be subjected to particle size distribution measurement by laser diffraction of suspended aerosol droplets and particles.

Preferably all high pressure parts are made from stainless steel. The restrictor length is preferably 2 in. (5 cm). Recent results prove that a longer restrictor (4 in. instead of 2 in.) gives similar results but with a decrease in flow rate of the supercritical fluid. This results, as shown by experiments involving pressure and flow rate variations described below, in a shift of the particle size distribution to different ranges depending on the conditions. The flow rates for the aqueous solutions in the above apparatus were 0.5 ml/min to 3 ml/min. If desired, the process may be conducted on a larger scale by adjusting dimensions and flow rates while maintaining similar temperatures and pressures.

Figure 2:
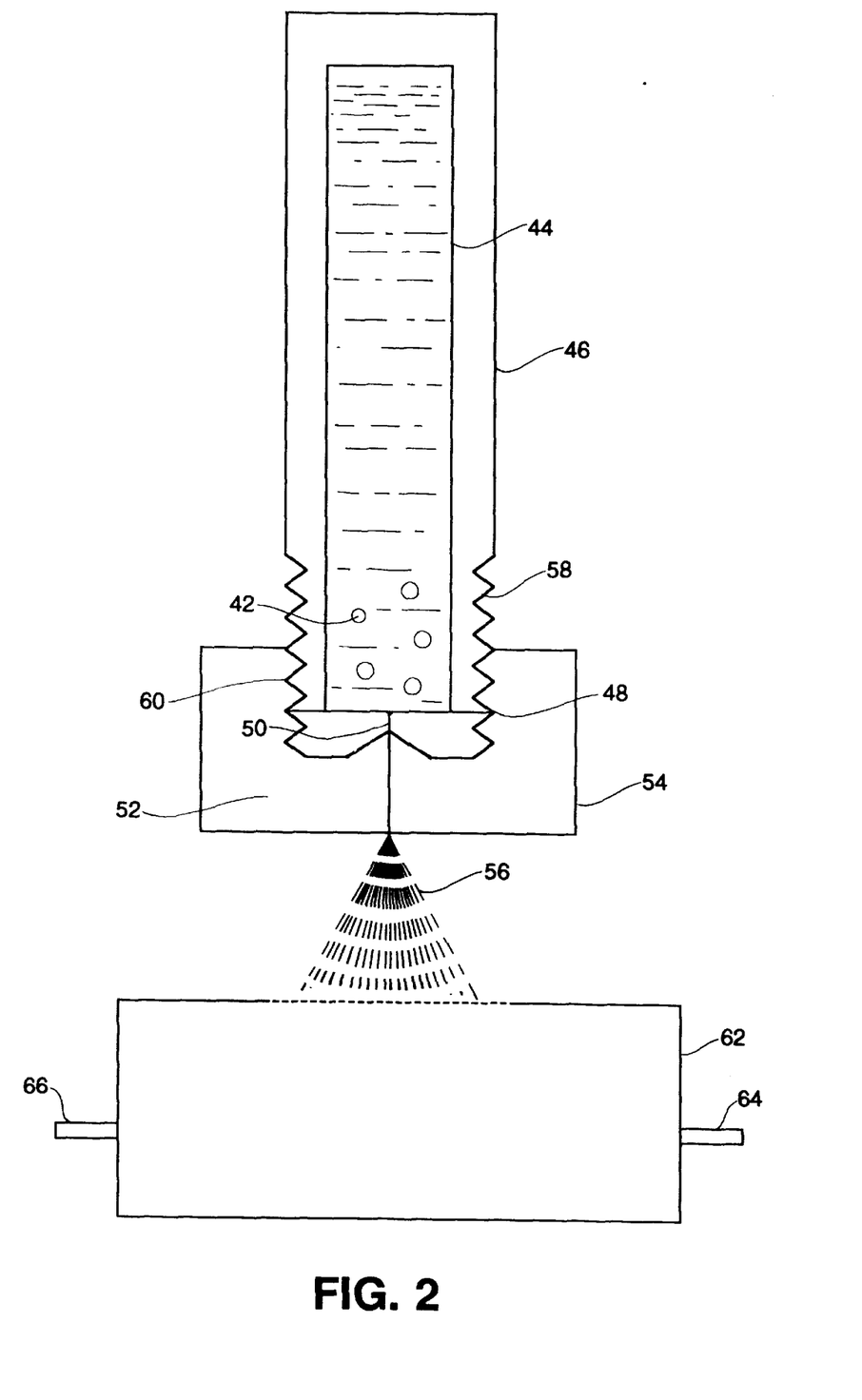
FIG. 2 is an apparatus of this invention which may be used for delivery of biologically active solutes to the lungs.

FIG. 2 shows an embodiment of this invention used for generation of fine particles from a static source such as a canister containing the immiscible mixture. This device comprises a canister 46, preferably of stainless steel comprising an immiscible mixture 44 of supercritical fluid and a solution or suspension of a substance equipped with a septum 48. The canister 46 is maintained above the critical pressure and temperature of the supercritical fluid. One or more stainless steel balls 42 are optionally added to facilitate mixing and emulsion formation by shaking. The septum is preferably a steel septum strong enough to withstand the pressure inside the canister 46. Puncturing pin 50 having a channel therethrough is placed adjacent to said septum 48. Puncturing pin 50 extends through orifice 52 in cap 54 which is preferably a stainless steel cap. Cap 54 is preferably threaded by means of threads 60 to screw onto the threaded end 58 of canister 46. Alternatively, a piercing plier can be used to rupture the septum, taking mechanical advantage of a lever rather than a screw.

In operation, cap 54 is screwed down onto canister 46 until puncturing pin 50 punctures septum 48, releasing the immiscible mixture 44 from canister 46 through orifice 52 into an area of ambient pressure. The rapid pressure release causes the formation of an aerosol comprising fine particles 56 of the desired substance suspended in the supercritical fluid. The particles are released into a bag, face mask, instrument inlet or reservoir 62. Air or other gases can be added through inlet 64 to dilute the aerosol. Outlet 66 conducts the aerosol to the atmosphere, or to delivery or measuring devices.

The most sensitive means for controlling particle size in the process of this invention is by varying concentration of the desired substance in the fluid used to solubilize it. The average particle size increases with increasing concentration of substances dissolved in water. In general, at a constant flow rate of the solution containing the desired substance, average particle size increases with a decrease in pressure of the supercritical fluid at high carbon dioxide pressures (around 1500 psi). At lower carbon dioxide pressures, e.g., 500, 750 and 1000, (under near-critical conditions) fine particles can also be generated. Near-critical fluids are defined (King, M. B., and Bott, T. R., eds. (1993), "Extraction of Natural Products using Near-Critical solvents," (Blackie Acad & Prof., Glasgow) pp. 1–33) as substances maintained at pressures between 0.9 and 1.0 of their critical pressure.

EXAMPLES

The apparatus of FIG. 1 was used to test the invention with respect to a number of dissolved substances. The mixing tee was heated to maintain the temperature of the mixture between 32° C. and 300° C. Typically 50° C. was used. The pressure of the two pumps was maintained above 1500 psi to keep both fluids in condensed states (liquid for aqueous solution and supercritical fluid for carbon dioxide). Typical flow rates were 0.1 to 3 cc/min of the aqueous solutions or suspensions and 0.3 to 10 cc/min of supercritical carbon dioxide. It should be noted that a 10:1 ratio of supercritical carbon dioxide to water is not sufficient to form a true solution in anywhere near the entirety of the water in the supercritical carbon dioxide (about 0.2–0.6 mole percent water in supercritical carbon dioxide is a saturated solution). Therefore, only about 6 mole percent of the aqueous solution could act as a true co-solvent, and the rest is an intimate two-phase mixture, perhaps a microemulsion. The result of expanding this mixture was, unexpectedly, copious amounts of fine particles (about 1 μm in diameter). Best results as regards particle size distribution were obtained using a flow rate of the aqueous solution of between 0.9 ml/min and 2 ml/min using a 127.5 μm restrictor. As will be appreciated by those skilled in the art, different restrictor sizes will require different flow rates of both fluids to maintain equivalent pressures. The pressure of the supercritical fluid was held constant at 1500 psi during the first experiments. The process involves many variables: as is appreciated by those skilled in the art, the pressure and type of supercritical fluid or gas and its flow rate, the flow rate of the aqueous solution and the length and inner diameter of the restrictor are dependent on each other such that a variation of one or more of these parameters will change others immediately. If, for example, the supercritical fluid pump controls the constant pressure of the supercritical fluid, a change in the flow rate of the aqueous solution will lead to an increase in back-pressure exhibited by the emulsion, and therefore to a decrease in the flow rate of the supercritical fluid and different compositions of the mixture. The concentration of the dissolved substance in the aqueous solution is an independent variable, however. As long as its concentration range is low enough that no significant change in the physical properties (e.g. viscosity) of the solution occurs by changing the concentration, the particle size distribution is directly dependent on the variation in concentration within the aqueous phase.

The examples show that the particle size distribution of aerosol particles formed by the new method favor generally smaller particles than other methods of aerosol generation. Abundant particles with diameters between 0.3 and 5 μm were formed, which is an optimal range for pulmonary drug delivery.

Example 1

Particle Size as a Function of Concentration

Figure 3:
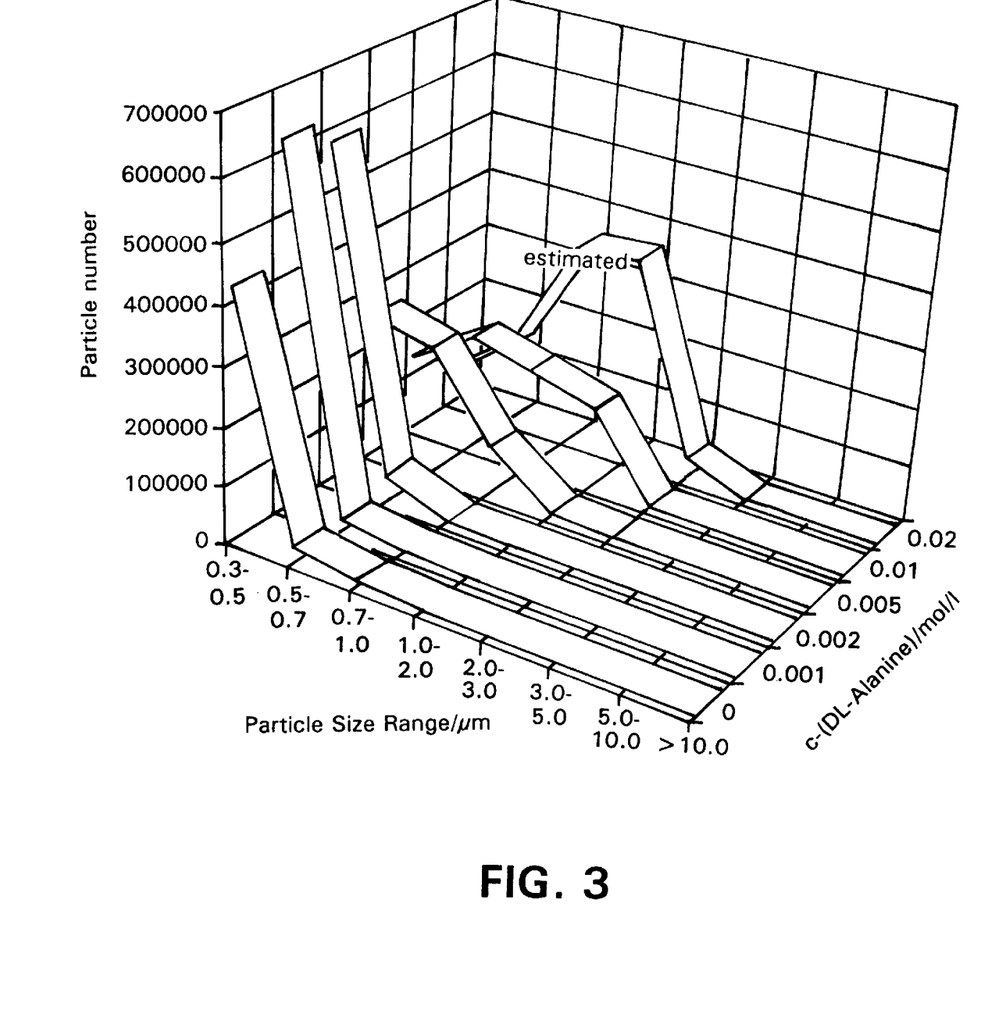
FIG. 3 is a graph showing particle size distribution as a function of concentration of alanine in aqueous solution in the process of this invention.

FIG. 3 shows the particle size distribution dependence on the concentration of alanine in aqueous solution using the experimental apparatus of FIG. 1. The alanine concentration was varied between 1 mmol/l and 20 mmol/l. A blank from water containing no added solute was included, referred to as the "water blank." Aerosol droplets were formed from the pure water, and changes in particle size and number were measured when the solute was present.

The flow rate of the aqueous solution was 0.9 ml/min and the pressure of the supercritical carbon dioxide was 1500 psi. The restrictor was heated in a water bath to 41° C. At 1 mmol/l, the number of particles in the size range 0.3–0.5 μm increased compared to the aerosol particles measured in the pure water blank. In all other size ranges, no significant change occurred. At the next concentration (2 mmol/l), the particle size distribution began to shift to larger particles with an increase of alanine concentration. As the absolute amount of substance in the solution increases, apparently separation of aggregates by a relatively smaller ratio of carbon dioxide to water is more difficult.

Figure 4:
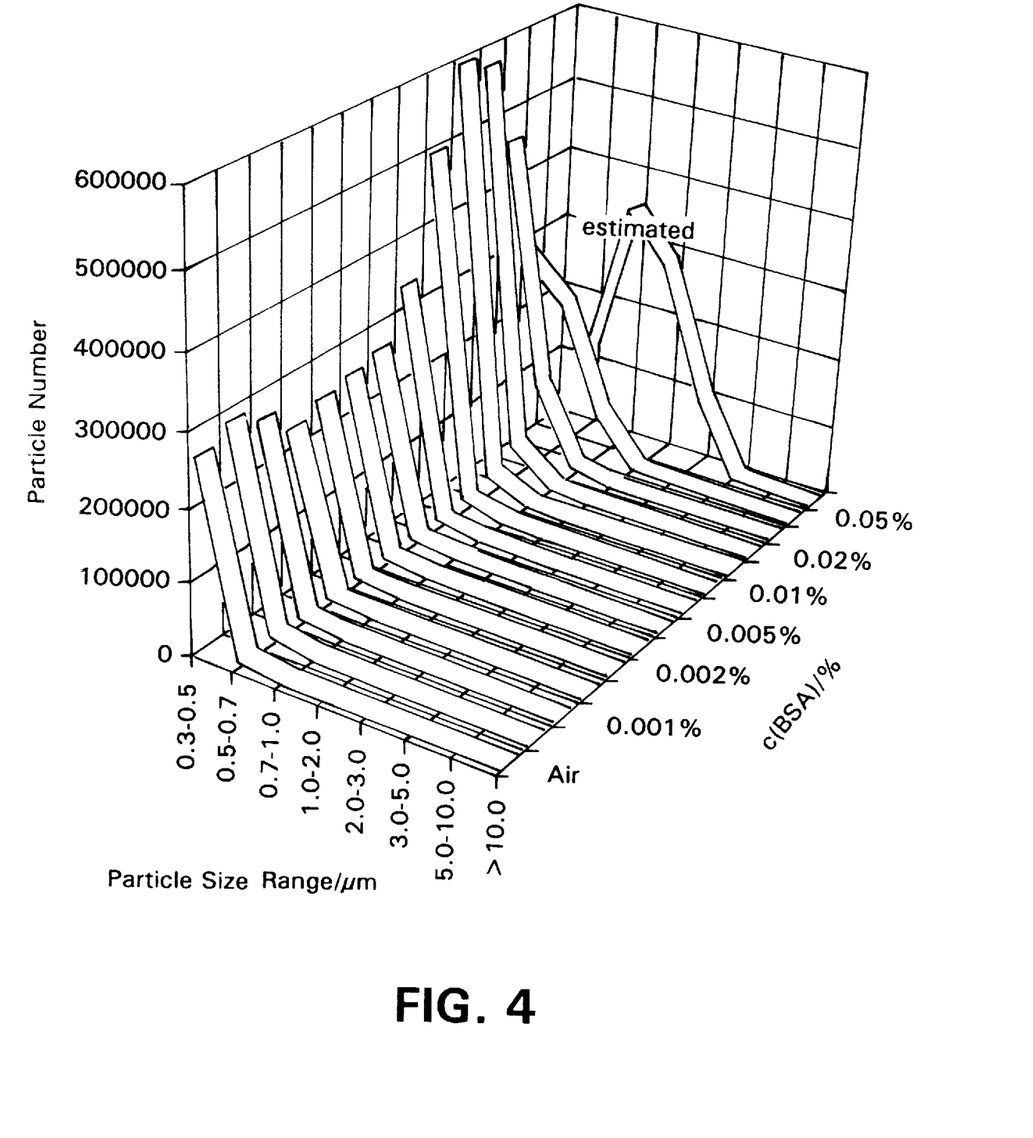
FIG. 4 is a graph showing particle size distribution as a function of concentration of bovine serum albumin (BSA) in aqueous solution in the process of this invention using smaller concentrations than shown in FIG. 4.

FIG. 4 shows particle size distribution dependence on the concentration of bovine serum albumin (BSA) in aqueous solution using the same conditions of flow rate, pressure and temperature. The first row is an "air blank" of the air in the hood surrounding the collector. This blank was much higher than usual on the day the tests reported here were performed. The second row shows a water blank. The lowest concentration of BSA studied here was 0.001% (w/v). In contrast to the alanine measurements shown in FIG. 3, the number of particles in the smallest size range first decreases with an increase in protein concentration. All other size ranges do not show any significant change. Beginning at 0.002% (w/v), the same shift to higher numbers of larger particles as with alanine is observed with an increase in concentration. An interpretation for these reproducible results with BSA might be that the absolute number of particles is increasing even at the very low concentrations. Nevertheless, the maximum of the size distribution could be well below 0.3 μm, the lower limit of the instrumental capability. As this effect was obtained in a similar way in the measurements with $Na_2Fe$ (DTPA), it is not believed specific for a particular substance and appears to be a general phenomenon.

Figure 5:
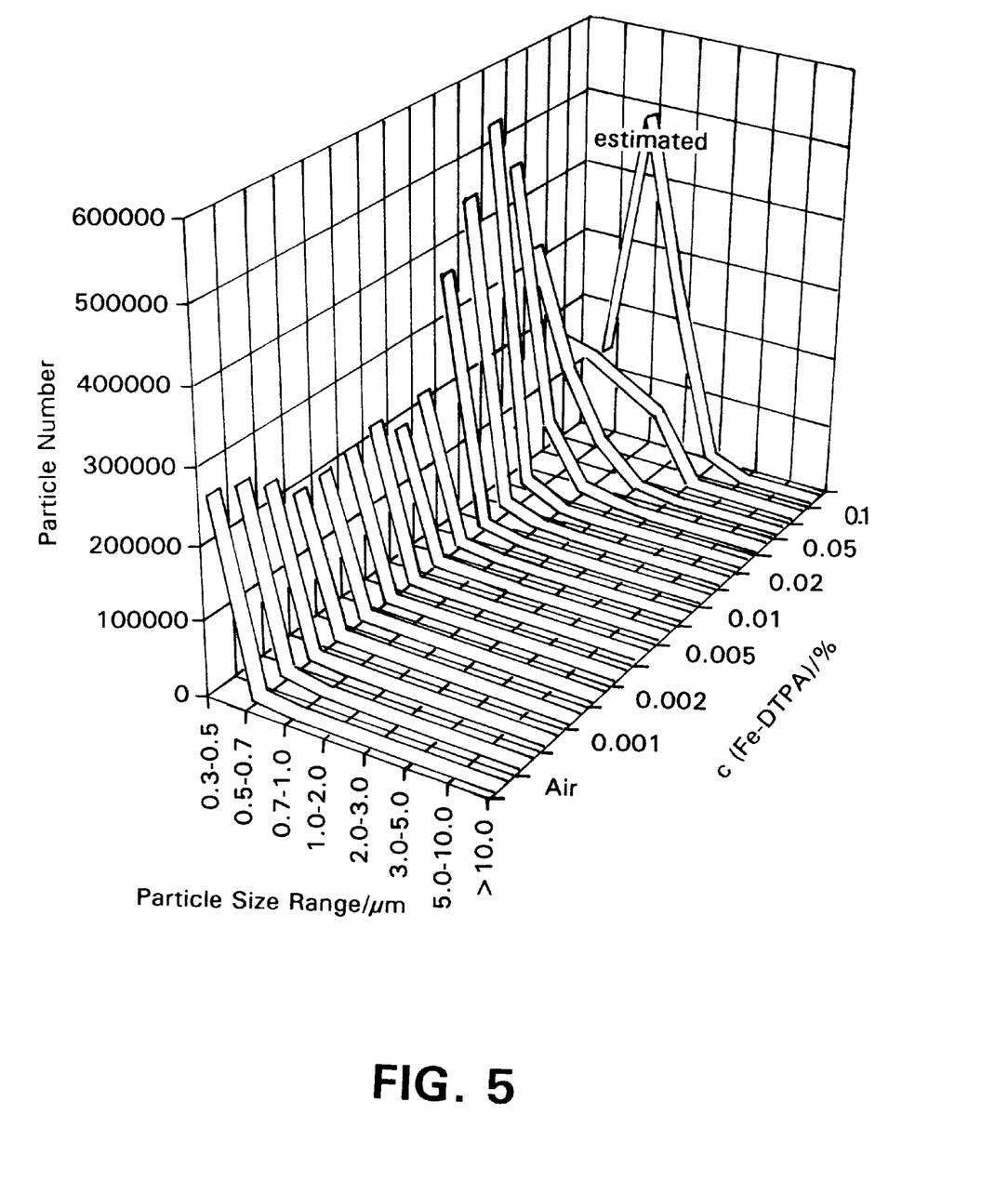
FIG. 5 is a graph showing particle size distribution as a function of concentration of disodium diethylenetriaminepentaacetato-iron(III) ($Na_2Fe(DTPA)$) complex in aqueous solution in the process of this invention.

FIG. 5 shows particle size distribution dependence on the concentration of $Na_2Fe(DTPA)$ using the same conditions of flow rate, pressure and temperature as used with alanine. Results are analogous to those achieved with BSA.

As the flow rates in these experiments are relatively high, the large number of particles generated can be detected. At higher concentrations of the model substances, the increase 
in particle number led to an overload of the particle size analyzer (in the size range 0.7 to 1.0 μm). Therefore, the number of particles in this range could only be estimated in this experiment. A further increase in concentration leads to breakdown of the size analyzer display. By extrapolation from the present results, higher concentrations should lead to larger average particle size.

Example 2

Particle Size as a Function of Temperature.

Carbon dioxide and nitrogen were used as carrier gases or supercritical fluids at 1500 psi and different restrictor temperatures in the range between 20° C. and 60° C. were used. Carbon dioxide is supercritical at temperatures of 31° C. and above at pressures above 1100 psi. Nitrogen is supercritical in the whole temperature and pressure range used here. In the experiment with carbon dioxide, we measured a strong change in the particle size distribution close to the critical temperature. With nitrogen there was only a small decrease in the average particle size with increasing temperature.

Even at subcritical conditions, the use of carbon dioxide results in smaller particle sizes than with nitrogen. A higher flow rate was used with nitrogen at a constant pressure than with carbon dioxide; however, the beneficial effects of using carbon dioxide may arise from the higher solubility of carbon dioxide in water compared to other gases. The solubility of carbon dioxide in water is between 2 and 3 mole percent between 80 and 200 atm at 15° C. to 25° C. (King, M. B. et al. (1992), "The Mutual Solubilities of Water with Supercritical and Liquid Carbon Dioxide," J. Supercrit. Fluids 5:296–302.) When the pressure is rapidly released on a small water droplet containing 2% carbon dioxide, abundant gas evolution may facilitate the formation of even smaller water droplets. The volume of gaseous carbon dioxide evolved is several-fold greater than the volume of the liquid droplets. There may also be some simultaneous drying of the fine particles to leave still finer particles of the solute or droplets of the solution. Therefore carbon dioxide is a preferred supercritical fluid. King et al. also report that the solubility of water in supercritical carbon dioxide at 15° C. to 40° C. is from 0.2 to 0.6 mole percent at pressures from 51 to 203 atm. This means that over a very wide ratio of carbon dioxide to water, the concurrent flow through the nozzle will be heterogeneous.

Without wishing to be bound by any theory of operation of the present invention, applicants suggest that some carbon dioxide becomes dissolved in the aqueous droplets together with the desired substance, while most of the carbon dioxide remains in the supercritical fluid state. When the pressure is released, both the supercritical carbon dioxide and the aqueous droplets expand, and the carbon dioxide in the liquid water droplets swells to burst the water droplets as they are being transported and diluted and dried in the surrounding dry air. The result is fine particles of the solute in an air-borne (or gaseous carbon dioxide-borne) dispersion.

Example 3

Use of Fine Aerosols Generated in Electrospray Mass Spectrometry.

Using a Sciex Model API3 (Toronto, Canada) triple quadruple mass spectrometer and the apparatus of FIG. 1 modified as described below, experiments were carried out using horse myoglobin dissolved in aqueous solution. This was mixed together with supercritical carbon dioxide for admission into the electrospray ionization nebulizer and charged tip source, with subsequent analysis of multiply charged myoglobin ions by the quadrupole mass spectrometer. A low dead volume stainless steel mixing tee was inserted at the inlet of the fused silica sampling capillary normally used with the Sciex Electrospray Ionization Sourt of the triple quadrupole mass spectrometer. One let of the tee received supercritical carbon dioxide and the second leg received the aqueous solution of the analyte from a high performance liquid chromatography pump, as in FIG. 1.

The main difference in procedure from the above experiments was that the restrictor capillary tip was electrically charged. The aerosols formed at the tip of the charged capillary were admitted into the mass spectrometer and analyzed. The result was an excellent mass spectrum with good signal to noise ratios even though an aqueous sample was being analyzed. Historically, solvents other than water have been chosen because unmodified aqueous solutions are too viscous to form fine droplets. The mass spectrum was quite different from that obtained with ordinary air nebulization of a methanol solution of horse myoglobin, possibly as a result of the carbon dioxide serving simultaneously as a modifier of viscosity and a nebulizing agent and participating in chemical ionization and/or affecting the protein chemically.

Results of these tests using horse myoglobin, a reference protein in mass spectrometry of larger biomolecules, showed very similar particle size distributions to those of Example 1 using BSA, which means the particles are finer than those of conventional nebulizers.

The flow rate of the aqueous solution was optimized at 10–100 μl/min for these experiments. The optimum pressure of the supercritical carbon dioxide was 3000 psi (flow rates approximately 300 μl/min). The restrictor used was a silica capillary with an inner diameter of 50 μm and a length of approximately 1.5 m Test results using the process of this invention are shown in Tables 1 and 2. Test results using standard techniques are presented in Table 3 for comparison.

TABLE 1*

| Actual peak | Intensity | Pred. peak | Charge | Compound mass |
|---|---|---|---|---|
| 925.70 | 460,000 | 925.44 | 19 | 17,569 |
| 977.00 | 600,000 | 976.80 | 18 | 17,567 |
| 1034.30 | 760,000 | 1034.20 | 17 | 17,565 |
| 1098.90 | 500,000 | 1098.78 | 16 | 17,566 |
| 1172.00 | 760,000 | 1171.96 | 15 | 17,564 |
| 1255.60 | 780,000 | 1255.60 | 14 | 17,564 |
| 1352.00 | 460,000 | 1352.11 | 13 | 17,562 |
| 1464.90 | 440,000 | 1464.70 | 12 | 17,566 |

Avg. compound mass 17,566.00
Std. Deviation: 1.99
8 Estimates of compound mass

TABLE 2*

| Actual peak | Intensity | Pred. peak | Charge | Compound mass |
|---|---|---|---|---|
| 808.30 | 940,000 | 808.17 | 21 | 16,953 |
| 848.60 | 2,080,006 | 848.53 | 20 | 16,951 |
| 893.20 | 3,040,000 | 893.14 | 19 | 16,951 |
| 942.70 | 3,580,000 | 942.70 | 18 | 16,950 |
| 998.20 | 3,000,000 | 998.09 | 17 | 16,952 |

TABLE 2*-continued

| Actual peak | Intensity | Pred. peak | Charge | Compound mass |
|---|---|---|---|---|
| 1060.60 | 1,840,000 | 1060.41 | 16 | 16,953 |
| 1131.10 | 2,400,000 | 1131.04 | 15 | 16,951 |
| 1211.70 | 1,260,000 | 1211.76 | 14 | 16,949 |
| 1304.90 | 1,100,000 | 1304.89 | 13 | 16,950 |
| 1413.60 | 660,000 | 1413.55 | 12 | 16,951 |

Avg. compound mass 16,951.56
Std. Deviation: 1.18
10 Estimates of compound mass

TABLE 3**

| Actual peak | Intensity | Pred. peak | Charge | Compound mass |
|---|---|---|---|---|
| 1352.40 | 900,000 | 1352.23 | 13 | 17,568 |
| 1464.80 | 2,660,000 | 1464.83 | 12 | 17,565 |
| 1597.90 | 4,120,000 | 1597.91 | 11 | 17,565 |
| 1757.60 | 4,700,000 | 1757.60 | 10 | 17,565 |
| 1952.90 | 2,380,000 | 1952.78 | 9 | 17,567 |
| 2196.40 | 920,000 | 2196.75 | 8 | 17,563 |

Avg. compound mass 17,565.92
Std. Deviation: 1.67
6 Estimates of compound mass
*Primary Charge Agent: H, 1.0079 mass, 1.0000 charge, Agent Gained
Tolerance for peak estimates: 0.50
Peak threshold: 358,000 (10.0%)
Minimum peak width: 0.40
Scan step size: 0.10
Number of peaks: 20
**Primary Charge Agent: H, 1.0079 mass, 1.0000 charge, Agent Gained
Tolerance for peak estimates: 0.50
Peak threshold: 470,000 (10.0%)
Minimum peak width: 0.40
Scan step size: 0.10
Number of peaks: 8

The foregoing description of the present invention has been directed to particular embodiments. It will be apparent, however, to those skilled in the art, that modifications and changes in both the apparatuses and the methods disclosed herein can be made without departing from the scope and spirit of the invention. It is the intention in the following claims to cover all such equivalent modifications and variations which fall within the true spirit and scope of this invention.

What is claimed is:

1. A device for making fine particles of a substance having an average diameter of less than about 6.5 $\mu$m comprising:
   (a) a first pressurized chamber containing a first nongaseous supercritical or near critical fluid;
   (b) a second chamber containing a solution or suspension of a substance in a second nongaseous fluid at least partially immiscible with said first fluid;
   (c) a mixing chamber for mixing said solution or suspension and first fluid connected to said first and second chambers by conduits;
   (d) first flow control means connected to the conduit between the first chamber and the mixing chamber for passing said first fluid into said mixing chamber;
   (e) second flow control means connected to the conduit between the second chamber and the mixing chamber for passing said second fluid into said mixing chamber so as to provide a composition within said mixing chamber comprising an at least partially immiscible mixture of said second fluid and said first fluid;
   (f) a restrictor for conducting the composition out of the mixing chamber into a rapid expansion region having a pressure below that of the supercritical or near-critical fluid where a dispersion of fine particles of said substance is formed.

2. The device of claim 1 wherein said mixing chamber is a low dead volume chamber.

3. The device of claim 1 also comprising a system for diluting said gas-borne dispersion with oxygen or air and administering said gas-borne dispersion to a target human or animal.

4. A device of claim 1 also comprising means for delivering fine particles to a target human or animal.

5. A device of claim 4 wherein said means for delivering fine particles to a target human or animal comprise a mouthpiece or face mask.

6. A device of claim 1 also comprising means for maintaining said first fluid in a supercritical state.

7. A device of claim 1 wherein said means for maintaining said first fluid in a supercritical state comprise a heater.

8. A device of claim 1 wherein said first fluid is supercritical carbon dioxide.

9. A device of claim 1 wherein said first fluid is a near-critical fluid.

10. A device of claim 1 wherein said first fluid is near-critical carbon dioxide.

11. A device of claim 1 wherein said second fluid is an aqueous fluid.

12. A device of claim 11 wherein said means for delivering fine particles to a target human or animal comprise a mouthpiece or face mask.

13. A device of claim 1 wherein said substance is a physiologically active composition selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, amino acids, peptides, proteins, enzymes, immune suppressants, thrombolytics, anticoagulants, central nervous system stimulants, decongestants, diuretic vasodilators, antipsychotics, neurotransmitters, sedatives, hormones, anesthetics, anti-inflammatories antioxidants, antihistamines, vitamins, minerals and other physiologically active materials known to the art.

14. A device for making fine particles of a substance having an average diameter of less than about 6.5 μm comprising:

(a) a substance:

(b) a pressurized chamber containing a non-gaseous supercritical or near-critical fluid;

(c) means to form a dispersion of fine particles of said substance by conducting through a restrictor into a rapid expansion region having a pressure below that of the supercritical or near critical fluid, a mixture of said non-gaseous supercritical or near-critical fluid and said substance dissolved or suspended in a second fluid, said second fluid being at least partially immiscible with said non-gaseous supercritical or near-critical fluid.

15. A device for making fine particles of a substance having an average diameter of less than about 6.5 μm comprising:

(a) a substance;

(b) means for contacting said substance with a first, nongaseous fluid to form a first solution or suspension;

(c) means for mixing said first solution or suspension with a second near-critical or supercritical fluid to form a composition comprising:

(1) said substance; and (2) an at least partially immiscible mixture of said first and second fluids; and (d) means for conducting said composition into a rapid expansion region having a pressure below that of the supercritical or near-critical fluid whereby said second fluid becomes a gas, and whereby a gas-borne dispersion of said fine particles of said substance is formed.

16. The device of claim 15 wherein said means for mixing comprises a low dead volume chamber.

17. A device for making fine particles of a substance having an average diameter of less than about 6.5 µm comprising:
   (a) a solution or suspension of a substance;
   (b) a pressurized chamber for contacting a supercritical or near-critical fluid with said solution or suspension to form a composition that is least partially immiscible, said solution or suspension comprising said substance in a carrier fluid; and
   (c) a restrictor for rapidly reducing the pressure on said composition into a rapid expansion region having a pressure below that of the supercritical or near-critical fluid so that said supercritical or near critical fluid becomes a gas, whereby a gas-borne dispersion of fine particles of said substance is formed.

18. The device of claim 17 wherein said restrictor comprises a nozzle.

19. A device for making fine particles of a substance having an average diameter of less than about 6.5 µm comprising:
   (a) a solution or suspension of a substance;
   (b) a chamber for contacting a supercritical or near-critical fluid with said solution or suspension to form a composition that is least partially immiscible, said solution or suspension comprising said substance in a carrier fluid; and
   (c) a restrictor comprising:
      (1) a pressure-resistant septum covering an orifice in said chamber;
      (2) a nozzle having a piercing end adjacent to said septum which operates to pierce said septum during use, said nozzle having a conduit therethrough; and
      (3) puncture forcing means for moving the piercing end of said nozzle through said septum;
   for conducting said composition into a rapid expansion region having a pressure below that of the supercritical or near-critical fluid so that the supercritical or near critical fluid becomes a gas, whereby a gas-borne dispersion of said fine particles of said substance is formed.

20. A device for making fine particles of a substance having an average diameter of less than about 6.5 µm comprising:
   (a) a chamber containing a mixture comprising:
      (1) a first fluid in which a substance is dissolved or suspended; and
      (2) a second supercritical or near-critical fluid at least partially immiscible with the first fluid;
   (b) means for conducting said mixture into a rapid expansion region having a pressure below that of the supercritical or near-critical fluid so that said supercritical or near critical fluid becomes a gas, whereby a suspension of fine particles of said substance in said gas is formed.

21. The device of claim 20, further comprising means for admitting said fine particles into a mass spectrometer for analysis.

22. The device of claim 20 wherein said second fluid is at least partially immiscible with said first fluid.

23. The device of claim 20 wherein said first fluid comprises water.

24. The device of claim 20, further comprising means for delivering fine particles to a target human or animal.

* * * * *